US012648933B2

(12) United States Patent
Nishida

(10) Patent No.: US 12,648,933 B2
(45) Date of Patent: Jun. 9, 2026

(54) PHARMACEUTICAL PREPARATION

(71) Applicant: KOWA COMPANY, LTD., Nagoya (JP)

(72) Inventor: Chisa Nishida, Fuji (JP)

(73) Assignee: KOWA COMPANY, LTD., Nagoya (JP)

( * ) Notice: Subject to any disclaimer, the term of this patent is extended or adjusted under 35 U.S.C. 154(b) by 1235 days.

(21) Appl. No.: 17/418,129

(22) PCT Filed: Dec. 27, 2019

(86) PCT No.: PCT/JP2019/051388
§ 371 (c)(1),
(2) Date: Jun. 24, 2021

(87) PCT Pub. No.: WO2020/138405
PCT Pub. Date: Jul. 2, 2020

(65) Prior Publication Data

US 2022/0054458 A1 Feb. 24, 2022

(30) Foreign Application Priority Data

Dec. 27, 2018 (JP) ................................ 2018-244285

(51) Int. Cl.
*A61K 47/38* (2006.01)
*A61K 31/423* (2006.01)

(52) U.S. Cl.
CPC ............ *A61K 31/423* (2013.01); *A61K 47/38* (2013.01)

(58) Field of Classification Search
CPC .................................................... A61K 31/423
See application file for complete search history.

(56) References Cited

U.S. PATENT DOCUMENTS

2005/0101636 A1 5/2005 Yamazaki et al.
2006/0189667 A1 8/2006 Yamazaki et al.
2010/0069433 A1 3/2010 Takizawa et al.
2015/0164809 A1* 6/2015 Nishida ................ A61K 9/2054 514/311
2016/0136138 A1 5/2016 Shibata et al.
2016/0354315 A1 12/2016 Li
2018/0028505 A1 2/2018 Oshima et al.
2018/0028506 A1 2/2018 Oshima et al.
2018/0311167 A1 11/2018 Li
2019/0192440 A1 6/2019 Li
2019/0321299 A1 10/2019 Li
2020/0121648 A1 4/2020 Minamizono
2020/0121649 A1 4/2020 Sugimoto et al.
2020/0121650 A1 4/2020 Sugimoto et al.
2020/0179346 A1 6/2020 Sugimoto et al.
2020/0222370 A1 7/2020 Kuroiwa et al.
2020/0315971 A1 10/2020 Li
2021/0077467 A1 3/2021 Oshima et al.
2021/0085652 A1 3/2021 Oshima et al.
2021/0089158 A1 3/2021 Oshima et al.
2021/0205226 A1 7/2021 Li

FOREIGN PATENT DOCUMENTS

EP 3 275 438 A1 * 7/2017
TW 200838510 A 10/2008
WO WO 2005/023777 A1 3/2005
WO WO 2015/005365 A1 1/2015
WO WO 2014/050134 A1 8/2016
WO WO 2016/192680 A1 12/2016
WO WO 2019/004447 A1 1/2019
WO WO 2019/004448 A1 1/2019
WO WO 2019/004451 A1 1/2019
WO WO 2019/004452 A1 1/2019
WO WO 2019/004453 A1 1/2019

OTHER PUBLICATIONS

Machine English translation of WO 2019/004453 (Sugimoto, et al.), publication date Mar. 1, 2019.*
Extended European Search Report issued on Jan. 2, 2023, in the European Application No. 19903282.2, 10 pages.
Anonimous: "This Report on the Deliberation Results". Jun. 13. 2017, XP055771515, Retrieved from the Internet: URL:https://www.pmda.go.jp/files/000226672.pdf[retrieved on Feb. 2, 2021].
Gajdosik Z., "Pemafibrate. Selective PPARalpha modulator, Treatment of dyslipidemia", Drugs of the future, vol. 41, No. 2. Jan. 1, 2016. XP055349188, ISSN 0377-8282, DOI: 10.1358/dof.2016.041.02.2412776, pp. 111-121.
International Search Report issued on Feb. 25, 2020 in PCT/JP2019/051388 filed on Dec. 27, 3 pages.
Yamazaki et al., "Enantioselective Synthesis of the PPARα Agonist (R)-K-13675 via (S)-2-Hydroxybutyrolactone", Synthesis, 2008, No. 7, pp. 1017-1022 (7 total pages).
Fruchart, "Selective peroxisome proliferator-activated receptorα modulators (SPPARMα): The next generation of peroxisome proliferator-activated receptor α-agonists", Cardiovascular Diabetology, 2013, vol. 12, No. 82, pp. 1-8.
"Report on the deliberation results of parmodia tablets 0.1 mg", Pharmaceutical Evaluation Division of Pharmaceutical Safety and Environmental Health Bureau, Ministry of Health, Labour and Welfare, 2017, 84 total pages (with partial English translation).
Combined Taiwanese Office Action and Search Report issued May 15, 2023 in Patent Application No. 108148156 (with English machine translation), 11 pages.

(Continued)

*Primary Examiner* — Shawquia Jackson
(74) *Attorney, Agent, or Firm* — Oblon, McClelland, Maier & Neustadt, L.L.P.

(57) ABSTRACT

[Problem] To provide a technique for suppressing the composition changes between pemafibrate, a salt thereof or a solvate thereof and an alkylcellulose species.

[Solving Means] A pharmaceutical preparation is provided by storing a pharmaceutical composition containing the following components (A) and (B) in a tight package: (A) pemafibrate, a salt thereof or a solvate thereof; and (B) an alkylcellulose species.

4 Claims, No Drawings

(56) References Cited

OTHER PUBLICATIONS

Notification of the new release of the hyperlipidemia treatment "Parmodia® Tablets 0.1mg," Kowa Company, Ltd., May 29, 2018, 3 pages.
Shun Ishibashi, et al., "Effects of K-877, a novel selective PPARα modulator (SPPARMα), in dyslipidaemic patients: A randomized, double blind, active- and placebo-controlled, phase 2 trial," Atherosclerosis, vol. 249, 2016, pp. 36-43.
Office Action issued Jan. 24, 2025, in corresponding Taiwanese Patent Application No. 108148156 (with English Translation), 8 pages.

* cited by examiner

PHARMACEUTICAL PREPARATION

This application is a national stage application of PCT/JP2019/051388, filed Dec. 27, 2019, which claims priority benefit of Japanese application 2018-244285, filed, Dec. 27, 2018, the contents of both applications are incorporated herein in their entirety.

FIELD OF THE INVENTION

The present invention relates to a pharmaceutical preparation etc.

BACKGROUND OF THE INVENTION

It is known that pemafibrate (Chemical Name: (2R)-2-[3-([1,3-Benzoxazol-2-yl[3-(4-methoxyphenoxy)propyl]amino]methyl)phenoxy]butanoic acid) (International Non-proprietary Name: pemafibrate) represented by the following structural formula:

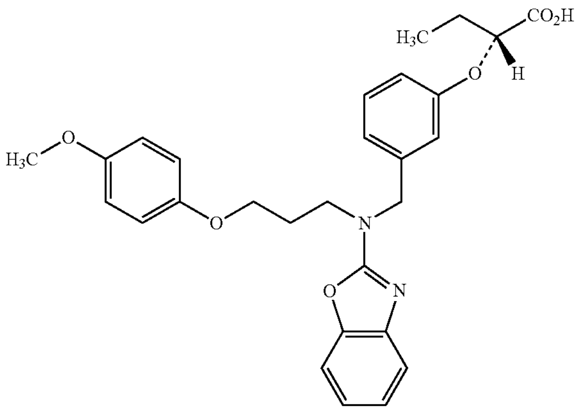

a salt thereof or a solvate thereof has excellent PPAR-α agonist activity, exhibits plasma triglyceride concentration reducing action, HDL cholesterol increasing action, etc., and is useful for prevention and treatment of dyslipidemia (hyperlipidemia) (Patent Document 1 and Non-Patent Documents 1 and 2), and useful for prevention and treatment of NAFLD (non-alcoholic fatty liver disease) (Patent Document 2).

Meanwhile, a compound useful as an active component for a pharmaceutical preparation is normally formulated as some pharmaceutical composition and administered, and it is not unusual that a long time passes until a pharmaceutical composition is administered after production of the pharmaceutical composition. Thus, from the viewpoint of exhibiting expected drug efficacy and avoiding unanticipated adverse side effects, it is very important to secure stability storage of active components in the pharmaceutical composition.

PRIOR ART DOCUMENTS

Patent Documents

Patent Document 1: International Publication No. WO 2005/023777

Patent Document 2: International Publication No. WO 2015/005365

Non-Patent Documents

Non-Patent Document 1: Yukiyoshi Yamazaki, et al., Synthesis, 2008 (7), 1017-1022.

Non-Patent Document 2: Fruchart J C., Cardiovasc Diabetol., 2013; 12:82.

SUMMARY OF THE INVENTION

Problems to be Solved by the Invention

However, storage stability of active components significantly depends on the physical and chemical properties of the components, and it is often impossible to predict such properties from the chemical structures or the like of the components, and there are not a few cases where a problem becomes evident only when a pharmaceutical composition is actually produced.

Pemafibrate, a salt thereof or a solvate thereof has been only reported to exhibit the above-described pharmacological effects, and has heretofore not been specifically studied in terms of a pharmaceutical composition, and storage stability in a pharmaceutical composition has heretofore not been reported at all. In addition to active components, various additives for pharmaceutical preparation are normally blended in a pharmaceutical composition.

In these circumstances, for developing a pharmaceutical composition containing pemafibrate, a salt thereof or a solvate thereof, the present inventor studied storage stability when various additives for pharmaceutical preparation are used. As a result, it was found that pemafibrate itself is very stable, but co-presence with an alkylcellulose species typified by ethylcellulose causes composition changes thereby bringing about a problem in storage that a mixture gets solidified over time.

Thus, an object of the present invention is to provide a technique for suppressing composition changes between pemafibrate, a salt thereof or a solvate thereof and an alkylcellulose species.

Means for Solving the Problems

The present inventor further extensively conducted studies in view of the aforementioned circumstances, and resultantly found that by storing a pharmaceutical composition containing pemafibrate, a salt thereof or a solvate thereof and an alkylcellulose species in a tight package such as a bottle package and a PTP package, it becomes possible to suppress composition changes. The present invention has been accomplished on the basis of this finding.

Accordingly, the present invention provides a pharmaceutical preparation obtained by storing a pharmaceutical composition comprising the following components (A) and (B) in a tight package:

(A) pemafibrate, a salt thereof or a solvate thereof; and (B) an alkylcellulose species.

The present invention also provides a method for stabilizing a pharmaceutical composition, the method comprising the step of storing a pharmaceutical composition comprising the following components (A) and (B) in a tight package:

(A) pemafibrate, a salt thereof or a solvate thereof; and (B) an alkylcellulose species.

Effects of the Invention

According to the present invention, it is possible to provide a pharmaceutical composition in which composition changes between pemafibrate, a salt thereof or a solvate thereof and an alkylcellulose species are suppressed to exhibit excellent storage stability.

DETAILED DESCRIPTION OF THE INVENTION

<Pemafibrate, Salt Thereof or Solvate Thereof>

Herein, "pemafibrate, a salt thereof or a solvate thereof" includes pemafibrate (Chemical Name: (2R)-2-[3-([1,3-Benzoxazol-2-yl[3-(4-methoxyphenoxy) propyl]amino] methyl) phenoxy]butanoic acid) (International Nonproprietary Name: pemafibrate) itself, a pharmaceutically acceptable salt of pemafibrate and a solvate of pemafibrate or a pharmaceutically acceptable salt thereof with water, alcohol (for example ethanol) or the like. The pharmaceutically acceptable salt is not particularly limited, and examples thereof include acid addition salts and base addition salts. Specific examples of the acid addition salts include acid addition salts with inorganic acids, such as hydrochlorides, hydrobromides, hydroiodides, sulfate salts, nitrate salts and phosphate salts; and acid addition salts with organic acids, such as benzoate salts, methanesulfonate salts, ethanesulfonate salts, benzenesulfonate salts, p-toluenesulfonate salts, maleate salts, fumarate salts, tartrate salts, citrate salts and acetate salts. Specific examples of the base addition salts include metal salts such as sodium salts, potassium salts, lithium salts, calcium salts and magnesium salts; salts with amines such as ammonia, trimethylamine, triethylamine, pyridine, collidine and lutidine; and base addition salts with organic bases such as lysine, arginine, cinchonine and cinchonidine.

Pemafibrate, a salt thereof or a solvate thereof is a known compound, and can be produced through a method as disclosed in Patent Document 1, Non-Patent Document 1 or U.S. Pat. No. 7,109,226, for example. In the present invention, a pemafibrate crystal which can be produced through the method described in Non-Patent Document 1 (preferably a crystal showing a melting point of 95 to 101° C., particularly preferably 97 to 100° C. in measurement performed in accordance with The Japanese Pharmacopoeia, 17th Edition, Melting Point Determination Method 1) is preferably used. The disclosures of the documents are incorporated herein by reference.

The content of pemafibrate, a salt thereof or a solvate thereof in the pharmaceutical composition is not particularly limited, and can be determined in appropriate consideration of the type of preparation, the sex, age and symptoms of a patient in need of the composition, and the like. For example, the content can be set so that the daily dose of pemafibrate, a salt thereof or a solvate thereof may be 0.05 to 0.8 mg, more preferably 0.075 to 0.6 mg, particularly preferably 0.1 to 0.4 mg, in terms of a free form of pemafibrate.

The content of pemafibrate, a salt thereof or a solvate thereof in the pharmaceutical composition is preferably 0.001 to 60 mass %, more preferably 0.0025 to 25 mass %, still more preferably 0.005 to 10 mass %, yet more preferably 0.0075 to 5 mass %, yet more preferably 0.01 to 1 mass %, particularly preferably 0.05 to 0.5 mass %, in terms of a free form of pemafibrate, with respect to the total mass of the pharmaceutical composition.

<Alkylcellulose Species>

Herein, the "alkylcellulose species" means one or more selected from the group consisting of a compound where all or a part of hydroxy groups of cellulose are each substituted with an alkoxy group and a salt thereof. The alkoxy group is preferably a linear or branched alkoxy group having 1 to 6 carbon atoms (more preferably 1 to 3 carbon atoms), such as methoxy group and ethoxy group. The salt is not particularly limited, and specific examples thereof include alkali metal salts such as sodium salts and potassium salts; and salts with metals of Group 2 elements, such as calcium salts and magnesium salts. The rate of alkoxy group substitution in the alkylcellulose species is preferably within a range of from 20 to 70%, more preferably within a range of from 40 to 60%. Determination of the rate of alkoxy group substitution in the alkylcellulose species is performed according to the determination method for methoxy group in a methylcellulose, as described in the Japanese Pharmacopoeia, 17th Edition. Additionally, the alkylcellulose species preferably has a viscosity of from 0.1 to 5000 mPa·s, more preferably from 1 to 200 mPa·s. Measurement of the viscosity of the alkylcellulose species is carried out according to the viscosity measurement method for methylcellulose, as described in the Japanese Pharmacopoeia, 17th Edition.

Specific examples of the alkylcellulose species include methylcellulose and ethylcellulose, and these may be used singly or in combination of two or more thereof. An alkyl group in the alkylcellulose species is not particularly limited but preferably a linear or branched alkyl group with 1 to 6 carbon atoms (more preferably 1 to 3 carbon atoms).

From the viewpoint of the effect of suppressing composition changes, the alkylcellulose species is preferably ethylcellulose.

All of these alkylcellulose species are known components, and may be produced by a known method, or commercial products may be used. Examples of such commercially available products include METOLOSE SM (Shin-Etsu Chemical Co., Ltd.), METOLOSE (San-Ei Gen F.F.I., Inc.), Methocel A (Dow Chemical Japan Limited), Ethocel (Dow Chemical Japan Limited), and Aquacoat (Asahi Kasei Corporation).

The content of the alkylcellulose species in the pharmaceutical composition is not particularly limited, and can be determined in appropriate consideration of the type of preparation, the sex, age and symptoms of a patient, and the like. From the viewpoint of the effect of suppressing the composition changes, it is preferably 0.001 to 55 mass %, more preferably 0.005 to 30 mass %, further preferably 0.01 to 20 mass %, particularly preferably 0.3 to 5 mass % with respect to the total mass of the pharmaceutical composition. Particularly in the case of using ethylcellulose as the alkylcellulose species, the content thereof is preferably 0.05 to 55 mass %, more preferably 0.075 to 15 mass %, further preferably 0.1 to 10 mass, much more preferably 0.5 to 3 mass % from the viewpoint of the effect of suppressing the composition changes.

The mass ratio between the content of pemafibrate, a salt thereof or a solvate thereof and the content of the alkylcellulose species in the pharmaceutical composition is not particularly limited, and from the viewpoint of the effect of suppressing the composition changes, the total content of the alkylcellulose species with respect to 1 part by mass of a free form of pemafibrate is preferably 0.001 to 500 parts by mass, more preferably 0.01 to 100 parts by mass, particularly preferably 0.5 to 50 parts by mass. Particularly when ethylcellulose is used as the alkylcellulose species, the content thereof is preferably 0.005 to 300 parts by mass, more preferably 0.01 to 75 parts by mass, particularly preferably 1 to 20 parts by mass with respect to 1 part by mass of a free form of pemafibrate from the viewpoint of the effect of suppressing the composition changes.

Herein, the dosage form of the "pharmaceutical composition" is not particularly limited, may be a solid, semisolid or liquid preparation, and can be selected according to the use purpose of the pharmaceutical composition. Examples of the dosage form of the pharmaceutical composition include dosage forms described in The Japanese Pharmacopoeia, 17th Edition, General Rules for Preparations. Specific examples of the peroral dosage form include solid preparations such as tablets (e.g. normal tablets, orally disintegrating tablets, chewable tablets, effervescent tablets, dispersion tablets, soluble tablets, and controlled-release tablets), capsules, granules (e.g. effervescent granules), powders and pills; semisolid preparations such as peroral jellies; liquid preparations such as peroral liquids (e.g. elixirs, suspensions, emulsions and lemonades). Examples of the parenteral dosage form include injections, inhalations, eye drops, ear drops, nasal drops, suppositories, solid external preparations, liquid external preparations, sprays, ointments, creams, gels and patches.

The pharmaceutical composition is preferably a solid preparation from the viewpoint of ease of administration and ease of production.

The solid preparation is preferably a peroral solid preparation, more preferably a tablet, a capsule, a granule, a powder or a pill, particularly preferably a tablet.

In addition to the above-described components, pharmaceutically acceptable carriers (additives for pharmaceutical preparation) may be added to the pharmaceutical composition for use in the present invention depending on its dosage form. Examples of the additives for pharmaceutical preparation include, but are not limited to, diluents, disintegrants, binders, lubricants, plasticizers, film formers, powders, poorly water-soluble polymer substances, antioxidants, flavors and sweetening agents. As specific examples of these additives for pharmaceutical preparation, those described in Japanese Pharmaceutical Excipients Directory 2016 (issued by Yakuji Nippo, Limited), Handbook of (issued by Pharmaceutical Excipients, Seventh Edition Pharmaceutical Press), etc. may be used.

Specific examples of the diluents include inorganic diluents such as aluminum silicate, anhydrous sodium sulfate, anhydrous dibasic calcium phosphate, sodium chloride, calcium silicate, light anhydrous silicic acid, heavy anhydrous silicic acid, calcium sulfate, calcium monohydrogen phosphate, dibasic calcium phosphate, dibasic sodium phosphate, monobasic potassium phosphate, monobasic calcium phosphate and monobasic sodium phosphate; and organic diluents such as corn syrup solids, caramel, agar, paraffin, sucrose, fructose, maltose, lactose, lactose monohydrate, white soft sugar, glucose, pullulan, polyoxyethylene hydrogenated castor oil, reduced maltose starch syrup, powdery reduced maltose starch syrup, trehalose, reduced palatinose, maltose, aminoalkyl methacrylate copolymer E, polyvinylacetal diethylaminoacetate and calcium citrate. These diluents may be used singly, or in combinations of two or more thereof.

The total content of the diluents is preferably 20 to 99 mass %, more preferably 30 to 95 mass %, with respect to the total mass of the pharmaceutical composition.

Specific examples of the disintegrants include gelatin, sodium hydrogen carbonate, dextrin, dehydroacetic acid and salts thereof, and polyoxyethylene hydrogenated castor oil 60. These disintegrants may be used singly, or in combinations of two or more thereof.

Specific examples of the binders include oils and fats such as tallow hydrogenated oil, hydrogenated oil, hydrogenated vegetable oil, soybean hydrogenated oil, carnauba wax, white beeswax, yellow beeswax and Japan wax, dextrin, pullulan, acacia, agar, gelatin, tragacanth, sodium alginate, polyvinyl alcohol, aminoalkyl methacrylate copolymer E and polyvinylacetal diethylaminoacetate. These binders may be used singly, or in combinations of two or more thereof.

The total content of the binders is preferably 0.001 to 30 mass %, more preferably 1 to 25 mass %, particularly preferably 2 to 20 mass %, with respect to the total mass of the pharmaceutical composition.

Specific examples of the lubricants include calcium stearate, magnesium stearate and sodium stearyl fumarate. Theses lubricants may be used singly, or in combinations of two or more thereof.

The total content of the lubricants is preferably 0.01 to 15 mass %, more preferably 0.1 to 10 mass %, with respect to the total mass of the pharmaceutical composition.

Specific examples of the plasticizers include triethyl citrate, sesame oil, castor oil and polysorbate 80 (polyoxyethylene(20)sorbitan oleate). These plasticizers may be used singly, or in combinations of two or more thereof.

The total content of the plasticizers is preferably 0.01 to 5 mass %, more preferably 0.1 to 1 mass %, with respect to the total mass of the pharmaceutical composition.

Specific examples of the film formers include alginic acid or salts thereof such as sodium alginate, carrageenan, xanthan gum and pullulan. These film formers may be used singly, or in combinations of two or more thereof.

Specific examples of the powders include organic and inorganic powders such as powders of talc, titanium oxide, yellow ferric oxide, red ferric oxide and legal color pigments. These powders may be used singly, or in combinations of two or more thereof.

The total content of the powders is preferably 0.005 to 3 mass %, more preferably 0.01 to 2 mass %, with respect to the total mass of the pharmaceutical composition.

Specific examples of the poorly water-soluble polymer substances include carboxyvinyl polymers and aminoalkyl methacrylate copolymers. These substances may be used singly, or in combinations of two or more thereof.

Specific examples of the antioxidants include ascorbic acid, sodium hydrogen sulfite, sodium sulfite, sodium edetate, erythorbic acid, tocopherol acetate, dibutylhydroxytoluene, natural vitamin E, tocopherol and butylhydroxyanisole. These antioxidants may be used singly, or in combinations of two or more thereof.

Specific examples of the flavors include terpenes such as limonene, pinene, camphene, cymene, cineole, citronellol, geraniol, nerol, linalool, menthol, terpineol, rhodinol, borneol, isoborneol, menthone, camphor, eugenol and cinnzeylanol; terpene-containing essential oils such as bitter orange oil, orange oil, peppermint oil, camphor white oil, eucalyptus oil, turpentine oil, lemon oil, ginger oil, clove oil, cinnamon oil, lavender oil, fennel oil, chamomile oil, fermented soybean oil and spearmint oil; and acidifiers such as ascorbic acid, tartaric acid, citric acid, malic acid and salts thereof. These flavors may be used singly, or in combinations of two or more thereof.

Examples of the sweetening agents include aspartame, stevia, sucralose, glycyrrhizic acid, thaumatin, acesulfame potassium, saccharin and saccharin sodium, and these sweetening agents may be used singly, or in combinations of two or more thereof.

The pharmaceutical composition for use in the present invention can be produced through a known method depending on its dosage form.

For example, the pharmaceutical composition, when it is a solid preparation, can be produced through appropriate combination of unit operations such as grinding, mixing, granulation, drying, grain size adjustment, classification, filling, palletizing and coating.

More specifically, for example, when the dosage form of the pharmaceutical composition is a granular preparation such as a granule, a powder or a pill, pemafibrate, a salt thereof or a solvate thereof and an alkylcellulose species, and additives for pharmaceutical preparation such as diluents, binders, disintegrants and lubricants are mixed in accordance with needs, the mixture is then granulated through a known granulation method such as extrusion granulation, tumbling granulation, agitation granulation, fluidized bed granulation, spray granulation, melt granulation or crushing granulation to obtain a granulated product, and the granulated product is subjected to classification, grain size adjustment and the like in accordance with needs, whereby the pharmaceutical composition can be produced. The obtained granulated product can be coated through a known method with a coating agent etc.

When the dosage form of the pharmaceutical composition is a tablet, pemafibrate, a salt thereof or a solvate thereof and an alkylcellulose species, and appropriate additives for pharmaceutical preparation such as diluents, binders, disintegrants and lubricants are mixed in accordance with needs to obtain a mixture, and the mixture is directly compressed (pelletized) (through a direct powder compression method), or compressed (pelletized) (through a semidry grain compression method, dry granule compression method, wet grain compression method or the like) after the above-described granulated product is subjected to classification, grain size adjustment and the like, whereby the pharmaceutical composition can be produced. The obtained compressed product (tablet) can be coated through a known method with a coating agent etc.

When the dosage form of the pharmaceutical composition is a capsule, the granulated product or compressed product may be capsulated.

Herein, the "tight package" means a package capable of suppressing entry of solid or liquid foreign matters in a state of normal handling, transportation, storage or the like, and includes the "tight container" and the "hermetic container" defined in The Japanese Pharmacopoeia, 17th Edition, General Rules. The tight package may be either shaped or unshaped, and specific examples of the tight package include bottle packages, strip packages (SP), press through packages (PTP), pillow packages and stick packages. The tight package may be a combination of two or more of these packages, and as a specific example, the pharmaceutical composition is first packed in a PTP package, and the PTP package is then packed in a pillow package.

The packaging material (raw material) for the tight package is not particularly limited as long as it can suppress the entry of solid or liquid foreign matters, and it is possible to appropriately use a material which is used for moisture-proofing of contents susceptible to moisture, etc. in the fields of pharmaceutical preparations, food products and the like, for example.

Examples of the material for the bottle body used for bottle packages include glass, plastics (polyester, polyethylene (including low-density polyethylene (LDPE), medium-density polyethylene (MDPE) and high-density polyethylene (HDPE)), polycarbonate, polystyrene, polypropylene, etc.), and metals (aluminum etc.). In preparation a bottle package, for example, an appropriate amount of the pharmaceutical composition may be stored in a commercially available bottle, followed by sealing the bottle with an appropriate cap or lid. As the bottle, one having a size suited for the amount etc. of the pharmaceutical composition to be stored may be appropriately selected, and the capacity of the bottle is, for example, about 10 to 500 mL, preferably 14 to 400 mL, more preferably 24 to 350 mL. The material for the bottle package is preferably glass, polyethylene or polypropylene, more preferably glass, low-density polyethylene (LDPE) or high-density polyethylene (HDPE), particularly preferably glass or high-density polyethylene (HDPE).

Examples of the packaging materials to be used for SP packages, PTP packages, pillow packages and stick packages include resins such as biaxially oriented polypropylene (OPP), biaxially oriented polyester (PET), glycol-modified PET (PET-G), biaxially oriented nylon (ONy, PA), cellophane, paper, low-density polyethylene (LDPE), linear low-density polyethylene (L-LDPE), ethylene-vinyl acetate copolymers (EVA), non-oriented polypropylene (CPP, IPP), ionomer resins (IO), ethylene-methacrylic acid copolymers (EMAA), polyacrylonitrile (PAN), biaxially oriented polyvinylidene chloride (PVDC), ethylene-vinyl alcohol copolymer resins (EVOH), polyvinyl chloride (PVC), cyclic polyolefins (COC), non-oriented nylon (CNy), polycarbonate (PC), polystyrene (PS) and rigid polyvinyl chloride (VSC); and metal foils such as aluminum foil (AL), and one or more of these materials may be appropriately combined to form a multilayer structure. Examples of the multilayer structure include laminates of PVC and PVDC (PVC/PVDC; hereinafter, structures are expressed in similar expressed forms), PVC/PVDC/PE/PVC, PVC/PVDC/PE/PVDC/PVC, CPP/COC/CPP, PVC/AL, CPP/AL and CPP/CPP/CPP. Examples of the method for forming such a multilayer structure include known lamination methods such as extrusion lamination, dry lamination, coextrusion lamination, thermal lamination, wet lamination, non-solvent lamination and heat lamination. As packaging materials to be used for SP packages, PTP packages, pillow packages and stick packages, polyvinyl chloride and aluminum foil are preferable.

As a form of the PTP package, one piece or one dosage unit of the pharmaceutical composition is stored in each of a desired number of pockets formed on a resin sheet etc. through a known method, and the pockets are then covered with a lid material which is a sheet formed of a metal foil such as aluminum foil. The PTP package may be a so-called PTP package with aluminum on both sides in which a sheet provided with pockets is also formed of aluminum foil. In the present invention, it is preferable to further pack the PTP package in a pillow package (e.g. aluminum pillow package) from the viewpoint of storage stability.

As a form of the SP package, pillow package or stick package, one piece or one dosage unit of the pharmaceutical composition is packed through a known method using a resin sheet, a sheet formed of aluminum foil, or the like. In the present invention, it is preferable to use a sheet formed of aluminum foil from the viewpoint of storage stability.

Herein, when the package is a bottle package, the occupancy (volume) of the pharmaceutical composition of the pharmaceutical preparation in the package is normally 25 to 90%, preferably 28 to 75%, more preferably 30 to 50%. When the package is an SP package, a PTP package, a pillow package or a stick package, the occupancy is normally 30 to 988, preferably 40 to 95%, more preferably 45 to 93%, particularly preferably 50 to 90%. In this case, the occupancy means an occupancy of the pharmaceutical composition with respect to the total volume of the inside of the package, and in calculation of the space occupancy, a pad, inside plug or the like for preventing breakage of the pharmaceutical composition stored in the package is not considered.

As the tight package, a commercially available package may be used as it is, or a commercially available packaging material may be processed and used. Examples of the commercially available package for bottle packages include Z-Series (manufactured by Hanshin Kasei Kogyo Co., Ltd.), A-Series (manufactured by ISOYA GLASS INDUSTRY) and the like. Examples of the packaging materials for SP packages, PTP packages, pillow packages and stick packages include SUMILITE VSS, SUMILITE VSL, SUMILITE NS and SUMILITE FCL (each manufactured by Sumitomo Bakelite Co., Ltd.), TAS Series (manufactured by Taisei Kako Co., Ltd.), PTP VINYFOIL and PTP SUPERFOIL (each manufactured by Mitsubishi Plastics, Inc.), NIPAK Aluminum Foil (manufactured by Nippon Foil Mgf. Co., Ltd.) and Aluminum Foil Silver Base (manufactured by Daiwa Chemical Industries Co., Ltd.).

The method for storing the pharmaceutical composition in the tight package is not particularly limited, and it is possible to arrange the pharmaceutical composition in the package through appropriate means for introducing the pharmaceutical composition into the package, etc. In this case, means for introducing a desiccant (e.g. columnar (tablet-shaped) or sheet-shaped desiccant) into the package together with the pharmaceutical composition may be used.

The disease to which the pharmaceutical preparation of the present invention is applied is not limited, and the pharmaceutical preparation can be widely used for prevention or treatment of diseases against which administration of pemafibrate is known or expected to be effective.

For example, pemafibrate, a salt thereof or a solvate thereof has excellent PPAR-α agonist activity, and exhibits plasma triglyceride concentration reducing action, HDL cholesterol increasing action, etc. Therefore, the pharmaceutical preparation of the present invention can be used preferably as an agent for prevention and/or treatment of dyslipidemia (hyperlipidemia, more specifically, for example primary hyperlipidemia and secondary hyperlipidemia), further preferably as an agent for prevention and/or treatment of hypertriglyceridemia, etc.

In addition, pemafibrate, a salt thereof or a solvate thereof is useful for prevention or treatment of NAFLD (non-alcoholic fatty liver disease). Therefore, the pharmaceutical preparation of the present invention can also be used as an agent for prevention and/or treatment of NAFLD (more preferably NASH (non-alcoholic steatohepatitis)), etc.

Further, pemafibrate, a salt thereof or a solvate thereof may be used as an agent for treatment of primary biliary cirrhosis, etc.

The administration route of the pharmaceutical composition for use in the present invention is not particularly limited, and can be determined in appropriate consideration of the target disease, the type of preparation, the sex, age, symptoms of a patient in need of the composition, and the like, but peroral administration is preferable from the viewpoint of ease of administration. The daily dose of the pharmaceutical composition can be taken as a single dose, or can be divided into 2 to 4 daily administrations (preferably taken as a single dose), and taken before each meal, between meals, after each meal, before bedtime, or the like.

For example, the following aspects are disclosed herein and should not be construed as limiting the present invention.

[1-1] A pharmaceutical preparation obtained by storing a pharmaceutical composition comprising the following components (A) and (B) in a tight package:

(A) pemafibrate, a salt thereof or a solvate thereof; and (B) an alkylcellulose species.

[1-2] The pharmaceutical preparation according to [1-1], wherein the component (B) is one or more selected from the group consisting of a compound where all or a part of hydroxy groups of cellulose are each substituted with a linear or branched alkoxy group having 1 to 6 carbon atoms and a salt thereof.

[1-3] The pharmaceutical preparation according to [1-1], wherein the component (B) is one or more selected from the group consisting of methylcellulose and ethylcellulose.

[1-4] The pharmaceutical preparation according to any one of [1-1] to [1-3], wherein the pharmaceutical composition is a solid preparation.

[1-5] The pharmaceutical preparation according to any one of [1-1] to [1-4], wherein the pharmaceutical composition is a tablet, a capsule, a granule, a powder or a pill.

[1-6] The pharmaceutical preparation according to any one of [1-1] to [1-5], wherein the tight package is one or more selected from the group consisting of a bottle package, an SP package, a PTP package, a pillow package and a stick package.

[1-7] The pharmaceutical preparation according to any one of [1-1] to [1-6], wherein the pharmaceutical preparation is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[2-1] A method for stabilizing a pharmaceutical composition, the method comprising the step of storing a pharmaceutical composition comprising the following components (A) and (B) in a tight package:

(A) pemafibrate, a salt thereof or a solvate thereof; and (B) an alkylcellulose species.

[2-2] The method according to [2-1], wherein the component (B) is one or more selected from the group consisting of a compound where all or a part of hydroxy groups of cellulose are each substituted with a linear or branched alkoxy group having 1 to 6 carbon atoms and a salt thereof.

[2-3] The method according to [2-1], wherein the component (B) is one or more selected from the group consisting of methylcellulose and ethylcellulose.

[2-4] The method according to any one of [2-1] to [2-3], wherein the pharmaceutical composition is a solid preparation.

[2-5] The method according to any one of [2-1] to [2-4], wherein the pharmaceutical composition is a tablet, a capsule, a granule, a powder or a pill.

[2-6] The method according to any one of [2-1] to [2-5], wherein the tight package is one or more selected from the group consisting of a bottle package, an SP package, a PTP package, a pillow package and a stick package.

[2-7] The method according to any one of [2-1] to [2-6], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[3-1] A pharmaceutical composition comprising the following components (A) and (B):

(A) pemafibrate, a salt thereof or a solvate thereof; and (B) an alkylcellulose species for storage in a tight package.

[3-2] The pharmaceutical composition according to [3-1], wherein the component (B) is one or more selected from the group consisting of a compound where all or a part of hydroxy groups of cellulose are each substituted with a linear or branched alkoxy group having 1 to 6 carbon atoms and a salt thereof.

[3-3] The pharmaceutical composition according to [3-1], wherein the component (B) is one or more selected from the group consisting of methylcellulose and ethylcellulose.

[3-4] The pharmaceutical composition according to any one of [3-1] to [3-3], wherein the pharmaceutical composition is a solid preparation.

[3-5] The pharmaceutical composition according to any one of [3-1] to [3-4], wherein the pharmaceutical composition is a tablet, a capsule, a granule, a powder or a pill.

[3-6] The pharmaceutical composition according to any one of [3-1] to [3-5], wherein the tight package is one or more selected from the group consisting of a bottle package, an SP package, a PTP package, a pillow package and a stick package.

[3-7] The pharmaceutical composition according to any one of [3-1] to [3-6], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

EXAMPLES

The present invention will next be described in detail by way of Examples, which should not be construed as limiting the invention thereto.

Test Example 1

Examination on Stability

Samples 1-1 to 1-4 as shown below were prepared and stored at 60° C. and 80% relative humidity (RH) for 21 days. Then, whether or not each of the samples exhibited a change between a state immediately after the start of storage and a state after storage for 21 days was evaluated, and additionally, the presence or absence of composition changes was determined.

Table 1 shows the results.

<Sample 1-1>

Pemafibrate as it was was placed in a glass vessel with a lid opened and labeled as Sample 1-1.

<Sample 1-2>

Ethylcellulose (ETHOCEL 10FP: Nisshin Kasei Co., Ltd.) as it was was placed in a glass vessel with a lid opened and labeled as Sample 1-2.

<Sample 1-3>

Ethylcellulose (ETHOCEL 10FP: Nisshin Kasei Co., Ltd.) was mixed with pemafibrate in a ratio of 1 part by mass to 1 part by mass of pemafibrate to obtain a mixture. The mixture was placed in a glass vessel with a lid opened and labeled as Sample 1-3.

<Sample 1-4>

Ethylcellulose (ETHOCEL 10FP: Nisshin Kasei Co., Ltd.) was mixed with pemafibrate in a ratio of 1 part by mass to 1 part by mass of pemafibrate to obtain a mixture. The mixture was taken in an amount of 0.25 g into a glass bottle (a bottle No. 2K, manufactured by ISOYA GLASS INDUSTRY) and closed with a lid, and labeled as Sample 1-4.

TABLE 1

| | | | State of mixture (60° C., 80% RH) | |
|---|---|---|---|---|
| Samples | Components | Storage in tight package | Immediately after the start of storage | 21 days later |
| 1-1 | Pemafibrate | Not done | White powder | White powder |
| 1-2 | Ethylcellulose | Not done | White powder | White powder |
| 1-3 | Pemafibrate + Ethylcellulose | Not done | White powder | Solidified white powder |
| 1-4 | Pemafibrate + Ethylcellulose | Done | White powder | White powder |

As is apparent from the test results shown in Table 1, Sample 1-1 (pemafibrate alone) and Sample 1-2 (ethylcellulose alone) that exhibited a state of white powder immediately after the start of storage maintained the same state even after the storage for 21 days. On the contrary, Sample 1-3 (a mixture of pemafibrate and ethylcellulose) caused a composition change and exhibited solidification of the mixture.

Meanwhile, in Sample 1-4 obtained by storing a mixture of pemafibrate and ethylcellulose in a tight package, it was found that the white powder state observed immediately after the start of storage was maintained even after the storage for 21 days.

The above test results reveal that composition changes between pemafibrate and an alkylcellulose species represented by ethylcellulose are suppressed by storage in a tight package.

Production Examples 1 to 6

Tablets (Examples 1 to 6) containing the components in the amounts (mg) thereof per tablet shown in Table 2 are conventionally produced and are stored in high-density polyethylene bottles to obtain pharmaceutical preparations of Production Examples 1 to 6, respectively.

TABLE 2

| | Amount blended (mg) (per tablet) | | | | | |
|---|---|---|---|---|---|---|
| Components | Example 1 | Example 2 | Example 3 | Example 4 | Example 5 | Example 6 |
| Pemafibrate | 0.1 | 0.2 | 0.4 | 0.6 | 0.2 | 0.4 |
| Lactose monohydrate | q.s. | q.s. | q.s. | q.s. | q.s. | q.s. |

TABLE 2-continued

| Components | Amount blended (mg) (per tablet) | | | | | |
|---|---|---|---|---|---|---|
| | Example 1 | Example 2 | Example 3 | Example 4 | Example 5 | Example 6 |
| Magnesium stearate | 1.2 | 1.2 | 1.2 | 1.2 | 1.2 | 1.2 |
| Methylcellulose | 0.02 | 4 | 8 | | | |
| Ethylcellulose | | | | 0.3 | 1 | 25 |
| Total | 100 | 100 | 100 | 100 | 100 | 100 |

The amount blended of pemafibrate in the table is a value calculated from the amount added.

Production Examples 7 to 12

Tablets (Examples 1 to 6) containing the components and the amounts (mg) thereof per tablet shown in Table 2 are conventionally produced and are placed in pocket portions formed on a resin sheet (SUMILITE VSS-1202 (trade name) manufactured by Sumitomo Bakelite Co., Ltd.) beforehand, and the pockets are then capped with PTP aluminum foil (Aluminum Foil Silver Base (trade name) manufactured by Daiwa Chemical Industries Co., Ltd.) to pack the tablets in a PTP package. 3 sheets of the obtained PTP package (each sheet contains 10 tablets) are further packed in an aluminum pillow package. Accordingly, pharmaceutical preparations of Production Examples 7 to 12, respectively, can be obtained.

Production Examples 13 to 18

Tablets (Examples 1 to 6) containing the components in the amounts (mg) thereof per tablet shown in Table 2 are conventionally produced and are placed in pocket portions formed on a resin sheet (SUMILITE VSS-1104 (trade name) manufactured by Sumitomo Bakelite Co., Ltd.) beforehand, and the pockets are then capped with PTP aluminum foil (Aluminum Foil Silver Base (trade name) manufactured by Daiwa Chemical Industries Co., Ltd.) to pack the tablets in a PTP package. 2 sheets of the obtained PTP package (each sheet contains 12 tablets) are packed in an aluminum pillow package. Accordingly, pharmaceutical preparations of Production Examples 13 to 18, respectively, can be obtained.

Production Examples 19 to 24

Tablets (Examples 1 to 6) are conventionally produced using the components in the amounts (mg) thereof per tablet shown in Table 2 and are placed in pocket portions formed on a resin sheet (SUMILITE VSL-4501 (trade name) manufactured by Sumitomo Bakelite Co., Ltd.) beforehand, and the pockets are then capped with PTP aluminum foil (Aluminum Foil Silver Base (trade name) manufactured by Daiwa Chemical Industries Co., Ltd.) to pack the tablets in a PTP package. 3 sheets of the obtained PTP package (each sheet contains 10 tablets) are packed in an aluminum pillow package. Accordingly, pharmaceutical preparations of Production Examples 19 to 24, respectively, can be obtained.

Production Examples 25 to 30

Tablets (Examples 1 to 6) containing the components in the amounts (mg) thereof per tablet shown in Table 2 are conventionally produced and are stored in a glass bottle. Accordingly, pharmaceutical preparations of Production Examples 25 to 30, respectively, can be obtained.

Production Examples 31 to 36

Tablets (Examples 1 to 6) containing the components in the amounts (mg) thereof per tablet shown in Table 2 are conventionally produced and are packed in an SP package with strip packaging aluminum foil (manufactured by Nissan Kako Co., Ltd.). Accordingly, pharmaceutical preparations of Production Examples 31 to 36, respectively, can be obtained.

INDUSTRIAL APPLICABILITY

The present invention enables provision of a pharmaceutical composition having excellent storage stability and containing pemafibrate which exhibits plasma triglyceride concentration reducing action, HDL cholesterol increasing action, etc. The pharmaceutical composition can be used in, for example, pharmaceutical preparation industries.

The invention claimed is:

1. A pharmaceutical preparation comprising:

(A) pemafibrate, a salt thereof or a solvate thereof; and (B) an alkylcellulose species comprising a cellulose with from 20 to 70% alkoxy group substitution of the hydroxy groups on the cellulose;

in a tight package selected from a tight container which is one or more selected from the group consisting of a bottle package, an SP package, a PTP package, a pillow package, and a stick package.

2. The pharmaceutical preparation according to claim 1, wherein the pharmaceutical composition is a solid preparation.

3. The pharmaceutical preparation according to claim 1, wherein the pharmaceutical composition is a tablet, a capsule, a granule, a powder, or a pill.

4. The pharmaceutical preparation of claim 1 wherein the rate of alkoxy group substitution in the cellulose is from 40 to 60%.

* * * * *